United States Patent
Stewart et al.

(10) Patent No.: US 6,660,531 B2
(45) Date of Patent: *Dec. 9, 2003

(54) RELAXIN LEVELS CORRLELATED TO IVF/ET PREGNANCY SUCCESS

(75) Inventors: Dennis R. Stewart, Sacramento, CA (US); Catherine A. VandeVoort, El Macero, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,981

(22) Filed: Jun. 22, 1998

(65) Prior Publication Data

US 2001/0053553 A1 Dec. 20, 2001

Related U.S. Application Data

(63) Continuation-in-part of application No. 08/879,662, filed on Jun. 23, 1997, now Pat. No. 5,994,148.

(51) Int. Cl.$^7$ ................... G01N 33/53; G01N 33/543; C07K 14/64
(52) U.S. Cl. ................. 436/510; 436/65; 530/399; 435/7.92
(58) Field of Search ................. 436/510, 501, 436/65; 530/399; 435/7.92

(56) References Cited

U.S. PATENT DOCUMENTS

| | | | |
|---|---|---|---|
| 3,845,770 A | 11/1974 | Theeuwes et al. | 128/260 |
| 3,995,651 A | 12/1976 | Adams | 137/38 |
| 4,034,756 A | 7/1977 | Higuchi et al. | 128/260 |
| 4,111,202 A | 9/1978 | Theeuwes | 128/260 |
| 4,320,759 A | 3/1982 | Theeuwes | 128/260 |
| 4,449,983 A | 5/1984 | Cortese et al. | 604/892 |
| 4,835,251 A | 5/1989 | Burnier et al. | 530/324 |
| 5,023,088 A | 6/1991 | Wong et al. | 424/473 |
| 5,166,191 A | 11/1992 | Cronin et al. | 514/12 |
| 5,451,572 A | 9/1995 | Cipolla et al. | 514/21 |
| 5,635,366 A | * 6/1997 | Cooke et al. | 435/26 |

FOREIGN PATENT DOCUMENTS

| | | |
|---|---|---|
| WO | WO 94/09805 | 5/1994 |
| WO | WO 94/21815 | 9/1994 |
| WO | WO 97/30175 | 8/1997 |

OTHER PUBLICATIONS

Wilcox et al. Defining and interpreting pregnancy success rates for in vitro fertilization. Fertil Steril. Jul. 1993;60(1):18–25.*

Weiss et al., Elevated first–trimester serum relaxin concentrations in pregnant women following ovarian stimulation predict prematurity risk and preterm delivery. Obstet Gynecol. Nov. 1993;82(5):821–8.

Stewart et al. "Relaxin as a biomarker for human pregnancy detection", pp. 214–224, in: Progress in relaxin research: 2nd International Congress on the Hormone Relaxin, MacLennan et al. (eds.), River Edge, N.J.: Global Publications Services, 1994.

Yding Andersen et al. Changes induced in serum protein profiles by ovarian stimulation during in–vitro fertilization—embryo transfer treatment: a comparison between conception and non–conception cycles. Human Reproduction, (May 1992) 7 (5) 585–91.*

Lee, Anne, et al., "Shark Cartilage Contains Inhibitors of Tumor Angiogenesis" *Science* (1983) 221:1185–1187.

Moses, Marsha A., et al., "Identification of an Inhibitor of Neovascularization from Cartilage" *Science* (1990), pp. 1408–1410.

Stewart, Dennis R., et al., "Relaxin in the Peri–Implantation Period" *J. Clinical Endocrinology and Metabolism* (1990) 70(6):1771–1773.

Stewart, Dennis R., et al., "The Relationship Between hCG and Relaxin Secretion in Normal Pregnancies vs Peri–Implantation Spontaneous Abortions" *Clinical Endocrinology* (1993) 38:379–385.

Stewart, Dennis R., et al., "Enhanced Ovarian Steroid Secretion before Implantation in Early Human Pregnancy" *J. Clinical Endocrinology and Metabolism* (1993) 76(6):1470–1476.

Stewart et al., "Relaxin secretion by human granulosa cell culture is predicative of IVF–ET pregnancy success." *Thirtieth Annual Meeting of the Society for the Study of Reproduction*, Portland, Oregon, U.S.A. Aug. 2–5, 1997, Biology Reproduction 56 (Suppl. 1) 1997.

Eddie et al., "Relaxin in Sera During the Luteal Phase of In Vitro Fertilization Cycles." *Br J Obstet Gynaecol* 97(3):215–220 (1990).

Bell et al., "Relaxin Levels in Antenatal Patients Following In Vitro Fertilizationn" *Fertil Steril* 52(1):85–87 (1989).

Bell et al., "Levels of Relaxin in In Vitro Fertilization Pregnancies in the First Trimester Measured with a Homologous Radioimmunoassay for Human Relaxin." *Fourth World Conference on In Vitro Fertilization*, Melbourne, Australia, Nov. 18–22, 1985, *J. In Vitro Fert Embryo Transfer* 3(3):184 (1986).

* cited by examiner

*Primary Examiner*—David S. Romeo
(74) *Attorney, Agent, or Firm*—Townsend and Townsend and Crew LLP

(57) ABSTRACT

A method of determining the probability of an in vitro fertilization (IVF) or embryo transfer (ET) method being successful is disclosed. Relaxin can be measured directly in the serum or indirectly by culturing granulosa lutein cells extracted from the patient as part of an IVF/ET procedure. A method of enhancing the rate of a successful pregnancy resulting from an IVF/ET procedure is also disclosed whereby relaxin is administered and/or endogenous relaxin levels are enhanced by varying convention IVF/ET procedures.

2 Claims, 10 Drawing Sheets

RELAXIN LEVELS CORRLELATED TO IVF/ET PREGNANCY SUCCESS

CROSS-REFERENCE

This application is a continuation-in-part application of Ser. No. 08/879,662, filed Jun. 23, 1997 now U.S. Pat. No. 5,994,148, which is incorporated herein by reference in its entirety and to which application we claim priority under 35 USC §120.

STATEMENT AS TO FEDERALLY SPONSORED RESEARCH

Material described in this application was supported in part by NIEHS POIES06198, RR 00169, and grant No. 5 P42 ES04699 from the National Institute of Environmental Health Sciences, NIH with funding provided by EPA. The Government may have certain rights in this invention.

FIELD OF THE INVENTION

The invention relates generally to the field of assays and methods of treatment. In particular the invention relates to determining relaxin levels and relating the levels to the probability of a successful fertilization of a human female and particularly success in an in vitro fertilization or embryo transfer procedure. The invention further relates to methods of enhancing the probability of obtaining a successful IVF/ET procedure.

BACKGROUND OF THE INVENTION

Reproductive failure is a serious problem that has been addressed clinically by in vitro fertilization (IVF) and embryo transfer (ET). These procedures might be expected to yield exceptionally high conception rates as in vitro fertilization provides an already fertilized ova for transfer into a fully primed recipient. Despite these efforts the success rate of IVF/ET is less than ideal. In the published data for IVF/ET in the United States and Canada in 1994, there were 26,961 initiated cycles of standard IVF. Of these, 86.2% led to a retrieval and of these 90.2% led to a transfer. However, the overall success rate in terms of clinical pregnancies was 22.7% per initiated cycle and a 29.1% pregnancy rate per transfer. Additionally, there appears to be a high incidence of early pregnancy loss after in vitro fertilization with a biochemical pregnancy rate of 18% and a spontaneous abortion rate of 27%. Thus, it appears that the IVF technique has been well optimized but implantation failure may be the cause for a large number of losses with ET and this implantational loss is an area of potential improvement.

The factors which contribute to the success of in vitro fertilization/embryo transfer (IVF/ET) have been extensively studied. In looking at what factors may affect implantation, many studies have reported correlations of hormonal or measurement of other parameters with conception rate. High conception rates have been associated with lowered follicular phase PP14 concentrations, large increases in PP14 concentrations from the day of human chorionic ganadotropin (hCG) stimulation to the day of embryo transfer, high preretrieval concentrations of CA-125, large increases in CA-125 from the day of hCG stimulation to oocyte retrieval, increased uterine blood flow, increased uterine artery impedance, and an inhibition of uterine motility in the periimplantation period. It has also been suggested that lowered estradiol concentrations at the time of ovulation induction lowered progesterone concentrations at the time of hCG stimulation, or the magnitude of the increase in progesterone in response to hCG stimulation have a higher success of conception. These reports generally fail to determine the mechanism by which these observations are translated into impaired conception.

Few studies have examined the relationship between granulosa lutein cell culture and the characteristics of the cycle from which cells were obtained. One group found that decreased granulosa cell 11 beta hydroxysteroid dehydrogenase activity was associated with higher conception rates. It was reasoned that exposure of the oocyte to cortisol was necessary for proper functional maturation and high amounts of enzyme in the cumulus cells could prevent this exposure. Another study was based upon observations that the magnitude of rise in progesterone concentrations in response to hCG stimulation was correlated with implantation success. They found that patients with an increase of 3 fold in response to hCG were more likely to get pregnant (46%) than those with a P4 increase of less than 3 fold who had only a 14% conception rate. Granulosa lutein cell culture (GLCC) from these patients showed differences in hormone production. Patients with a large serum P4 increase had higher progesterone concentrations in culture. Patients with a low P4 increase had more variable estrogen concentrations in culture but the estrogen was more responsive to gonadotropin stimulation.

SUMMARY OF THE INVENTION

A method of predicting the probability of a successful pregnancy resulting from in vitro fertilization (IVF) or embryo transfer (ET) based on relaxin levels is disclosed. The relaxin levels may be determined by culturing granulosa lutein cells (preferably for ten days) extracted from the patient as part of the IVF/ET procedures and/or by measuring relaxin levels in serum. A method of enhancing the rate of successful term pregnancy is provided by administering relaxin in amounts sufficient to raise relaxin levels and/or by modifying conventional procedures so as to increase endogenous relaxin.

An aspect of the invention is to provide a method of determining the probability of obtaining successful in vitro fertilization or embryo transfer.

Another aspect is to determine relaxin concentration of cultured granulosa lutein cells at about 10 days after extraction and relating the level to a standard to determine the probability of a successful IVF/ET procedure.

Another aspect is to determine relaxin levels in serum and relate the level directly to IVF/ET success probability or indirectly by first relating such to relaxin levels of cultured granulosa lutein cells.

Another aspect of the invention is to provide a method for determining the success rate for IVF/ET procedures by assaying for levels of glycodelin, specifically glycodelin released from the endometrium.

Yet another aspect of the invention is to measure levels of hCG and relate the levels to a standard which relates to relaxin levels thereby determining the probability of success with IVF/ET procedures.

Yet another aspect of the invention is to provide a method for predicting the success of an IVF/ET procedure by measuring levels of relaxin, glycodelin, hCG in any combination and relating those levels to a standard.

Yet another aspect of the invention is to provide a method for enhancing the success rate of an IVF/ET procedure by administering into a patient any of relaxin, glycodelin or hCG.

Another aspect is to provide a method for enhancing the success rate for IVF/ET procedures by modifying aspects of conventional procedures to increase endogenous relaxin levels at crucial time periods.

An advantage is that measured relaxin levels are predictive of success rates for conception and for obtaining a term pregnancy.

The assay of the invention shows that relaxin levels at 800 pg/ml or more are highly predictive of resulting in a successful pregnancy.

A feature of the invention is that it requires measurement of only a single hormone.

These and other aspects, advantages and features of the invention will become apparent to those skilled in the art upon reading the disclosure.

DEFINITIONS

Figure 1:
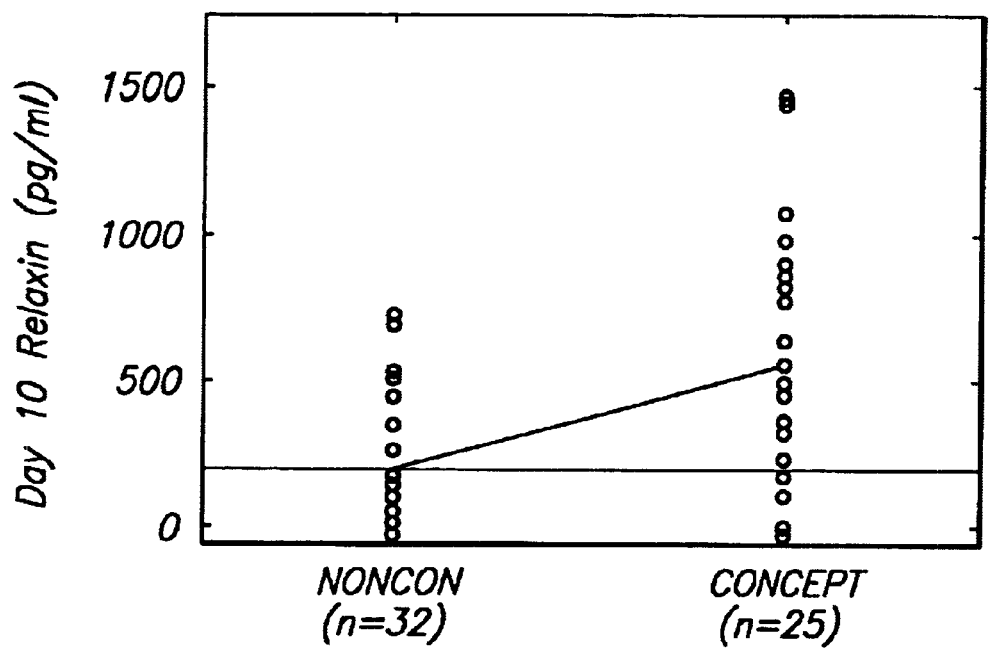
FIG. 1 is a graph showing relaxin concentration on day 10 of cultured granulosa cells from 57 human female patients grouped based on whether conception occurred where n is the number of patients and the line connects the mean value in each group.

The term "relaxin" refers to mature human relaxin which is a hormone peptide of approximately 6,000 daltons which can be made by processes described in U.S. Pat. No. 4,835,251 and (PCT US94/0699). Methods of using relaxin in cardiovascular therapy and in the treatment of neurodegenerative diseases are described in U.S. Pat. No. 5,166,191 and in (PCT US92/06927). Certain formulations of human relaxin are described in U.S. Pat. No. 5,451,572, issued Sep. 19, 1995, incorporated to disclose and describe such formulations as well as methods of administration and dosing.

The terms "conception", "conceptive" and the like as used herein refers to detecting hCG in serum after a IVF/ET procedure and nonconceptive refers to the absence of detectable endogenous hCG in serum after the hCG used to stimulate ovulation clears from the blood.

The term "successful IVF/ET procedure" means conception resulted from a IVF/ET procedure and preferably went to term.

"Optional" or "optionally" means that the subsequently described event or circumstance may or may not occur, and that the description includes instances where said event or circumstance occurs and instances in which it does not.

The terms "treatment", "treating", "treat" and the like are used herein to generally mean obtaining a desired pharmacologic and/or physiologic effect which enhances the likelihood of conception and preferably enhances the likelihood of a term pregnancy. The effect may be prophylactic in terms of completely or partially preventing a reaction or situation which hinders or prevents conception and/or may be therapeutic in terms of a partial or complete elimination of an adverse effect which hinders conception or pregnancy. "Treatment" as used herein covers any treatment of any physiological condition in a mammal, particular a human female, and includes:

(a) preventing the condition such as infertility from occurring in a subject which may be predisposed to the condition but has not yet been diagnosed as having it;

(b) inhibiting the condition (e.g., infertility), i.e., arresting its development; or (c) relieving the condition, i.e., causing regression of the condition (successful pregnancy).

The term "effective amount" means a dosage sufficient to provide treatment for the condition disease state being treated, e.g., infertility. This will vary depending on the patient, the condition, e.g., the type of infertility and the treatment being effected. In the case of pregnancy, an "effective amount" is that amount necessary to substantially improve the likelihood of successful pregnancy, in particular that amount which improves the likelihood of successfully completing the first trimester, and especially of successfully causing the embryo to implant. An effective amount should be sufficient to achieve a successful result in at least 65% of the pregnancies tested, more preferably in at least 75%, still more preferably at least 85%, and most preferably should provide for a successful implantation in at least 95% of the occasions administered, in the absence of other complicating factors. The dosage administered may be adjusted based on the level of relaxin measured in the particular patient being treated.

The terms "standard", "standard level", "standardized relaxin level" and the like are used interchangeably herein to define a determined concentration of relaxin obtained from taking a number of readings-preferably a statistically significant number of readings. The standard can be arbitrarily fixed depending on the level of success a reading above or below the standard is to indicate. Based on present data a culture level at day 10 above 800 pg/ml would appear to indicate a 100% chance of success. The percentage would be expected to decrease when larger numbers of patients are tested.

IVF stands for in vitro fertilization and specifically to such a procedure on a human female.

ET stands for embryo transfer and specifically to the transfer of a human embryo.

hCG stands for human chorionic ganadotropin.

GLCC stands for granulosa lutein cell culture.

Responder refers to obtaining a relaxin concentration of >200 pg/ml after a 10 day culture of GLCC at a standard hCG dose of 0.02 IU/ml.

Non-responder refers to obtaining a relaxin concentration of <200 pg/ml after a day culture of GLCC at a standard hCG dose of 0.02 IU/ml.

DETAILED DESCRIPTION OF PREFERRED EMBODIMENTS

Before the present assays and methods are disclosed and described, it is to be understood that this invention is not limited to particular assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

VARIABILITY OF RELAXIN LEVELS

The present invention includes a cell culture system for human luteinizing granulosa cells which supports the timely and dynamic secretion of estrogen (E2), progesterone (P4) and relaxin in patterns that mimic serum patterns of secretion of these hormones during the luteal phase of the menstrual cycle. The results obtained provide a profile of relaxin secretion similar to that of a normal nonconceptive menstrual cycle. The results also show that the amount of relaxin produced from cells taken from different human female patients is highly variable from human to human. Relaxin production on day 10 of culture ranged from 1500 pg/ml to undetectable in cultures from different patients. Those patients showing a relaxin level above 800 pg/ml showed 100% success rate and those showing levels below 200 pg/ml showed a 6.7% success rate. The result also shows that for the same patient at the same time the relaxin levels in the cells culture correlate to the levels in serum.

Figure 2:
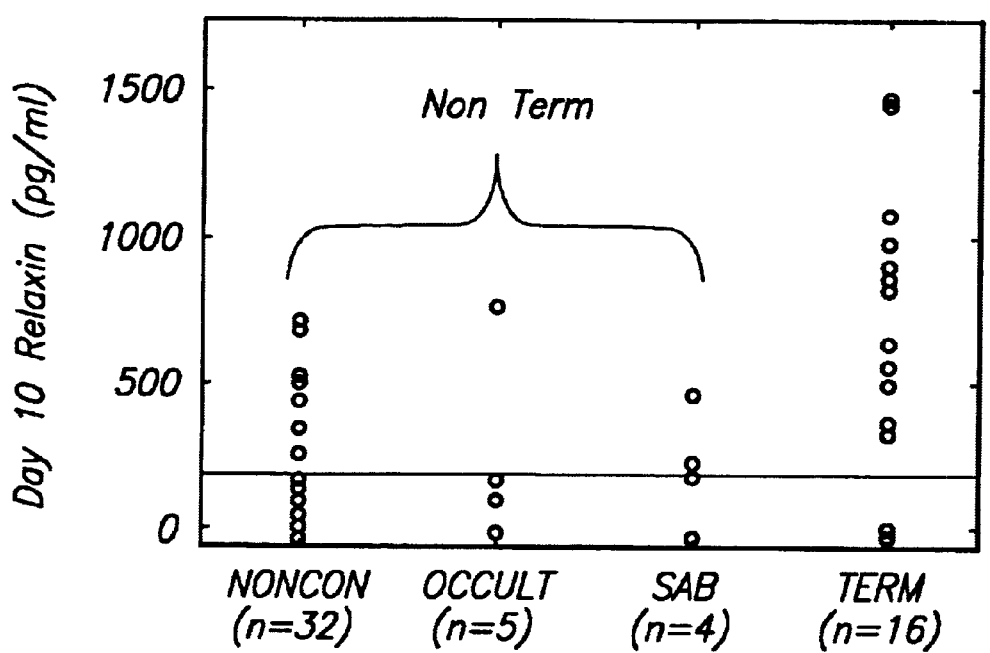
FIG. 2 is a graph showing relaxin concentration on day 10 of cultured granulosa cells with the patients grouped by (a) no conception; (b) occult-pregnancy ended soon; (c) spontaneous abortion; and (d) term deliveries.
Figure 3:
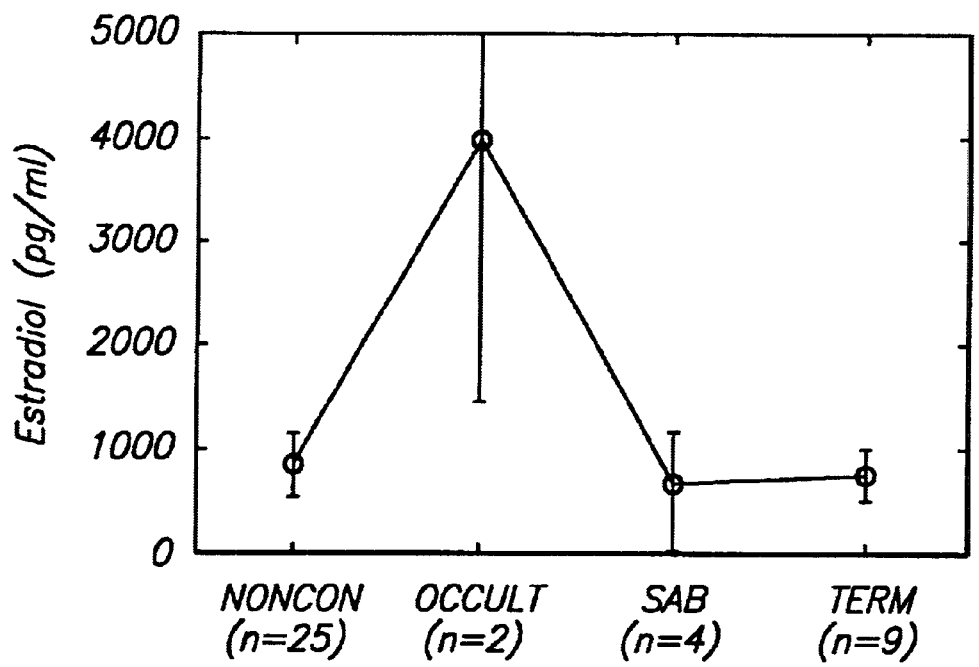
FIG. 3 is a graph showing the mean estradiol concentration of all patients in the group on day 10 of cultured granulosa cells with the patients grouped by (a) no conception; (b) occult; (c) spontaneous abortion; and (d) term deliveries.
Figure 4:
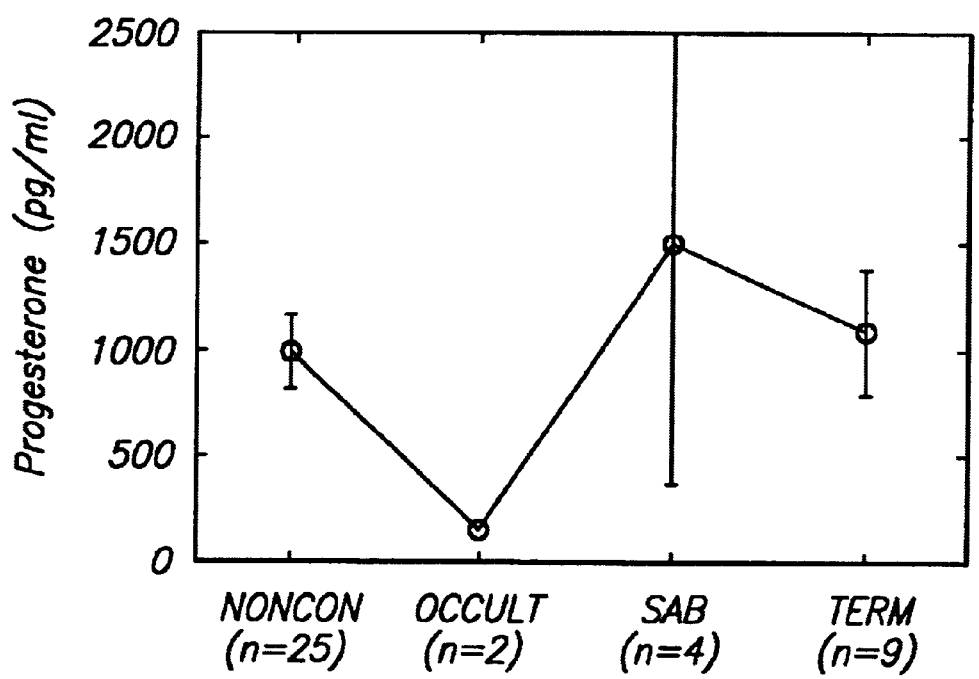
FIG. 4 is a graph showing the mean progesterone concentration of all patients in the group on day 10 of cultured granulosa cells with the patients grouped by (a) no conception; (b) occult; (c) spontaneous abortion; and (d) term deliveries.

The magnitude of relaxin secretion during the middle of granulosa lutein cell culture is significantly correlated with pregnancy success (see FIGS. 1, 2 and 5) while estradiol and progesterone production is not (see FIGS. 3 and 4). This shows that relaxin is involved in the normal implantation process and that lowered relaxin concentrations result in poor IVF/ET pregnancy rates.

In examining the endocrine responses from granulosa lutein cells in culture, it was noted that there was an excellent correlation of relaxin concentrations during the middle of the culture period (day 10) and the detection of conception in the cycle from which the cells were obtained. Few cycles with low relaxin from the cell culture showed signs of implantation or had a successful pregnancy while cycles with high relaxin had a high rate of conception (see FIGS. 1 and 5). This relationship shows that increasing relaxin levels can enhance the probability of a successful IVF/ET procedure. Relaxin levels can be increased by (1) administration of exogenous relaxin, (2) manipulating IVF/ET procedure to enhance endogenous relaxin or (3) as combination of (1) and (2).

Table 1 is divided arbitrarily into two sections with the first showing relaxin levels below 200 pg/ml (non-responders) with thirty patients and the second portion showing relaxin levels above 200 pg/ml (responders) with twenty-seven patients.

TABLE I

| Subject | Age | GLCC Relaxin | Pregnancy |
|---|---|---|---|
| *Non-Responders* | | | |
| 1 | | −23 | − |
| 2 | 36 | −22 | + |
| 3 | 28 | −21 | + |
| 4 | 38 | −14 | − |
| 5 | 40 | −13 | − |
| 6 | 29 | −9 | − |
| 7 | 31 | −6 | − |
| 8 | | −4 | + |
| 9 | 37 | 0 | − |
| 10 | 28 | 3 | + |
| 11 | 37 | 18 | − |
| 12 | 36 | 19 | − |
| 13 | 36 | 37 | − |
| 14 | 34 | 48 | − |
| 15 | 41 | 68 | − |
| 16 | 37 | 111 | + |
| 17 | 34 | 111 | − |
| 18 | 33 | 112 | − |
| 19 | 30 | 146 | − |
| 20 | 39 | 149 | − |
| 21 | 34 | 151 | − |
| 22 | 39 | 155 | − |
| 23 | 39 | 159 | − |
| 24 | 38 | 159 | − |
| 25 | 34 | 164 | − |
| 26 | 39 | 174 | + |
| 27 | 35 | 179 | − |
| 28 | 31 | 184 | + |
| 29 | 37 | 191 | − |
| 30 | | 196 | − |
| MEAN | 35.2 | 80.9 | 23− 7+ |
| *Responders* | | | |
| *Relaxin above 200 pg/ml* | | | |
| 31 | 38 | 235 | + |
| 32 | 32 | 273 | − |
| 33 | 38 | 324 | + |
| 34 | 33 | 328 | + |
| 35 | | 358 | − |
| 36 | 37 | 365 | + |
| 37 | | 457 | − |
| 38 | 36 | 464 | + |
| 39 | 34 | 496 | + |
| 40 | 37 | 517 | − |
| 41 | 30 | 526 | − |
| 42 | 37 | 544 | − |
| 43 | 35 | 558 | + |
| 44 | 30 | 637 | + |
| 45 | 37 | 700 | − |
| 46 | 34 | 723 | − |
| 47 | 26 | 736 | − |
| 48 | 32 | 768 | + |
| 49 | 32 | 781 | + |
| 50 | 39 | 823 | + |
| 51 | 32 | 857 | + |
| 52 | 39 | 898 | + |
| 53 | 27 | 905 | + |
| 54 | | 983 | + |
| 55 | | 1075 | + |
| 56 | 44 | 1453 | + |
| 57 | | 1470 | + |
| MEAN | 34.5 | 676.5 | 9− 18+ |

The results shown in Table I are summarized below in Table II showing that 18 of 27 patients (66.7%) in the higher relaxin level group conceived whereas only 7 of the 30 (23.3%) patients in the lower relaxin level group conceived.

TABLE II

| Relaxin | NonConceptive | Conceptive |
|---|---|---|
| >200 pg/ml | 9 | 18 |
| ≦200 pg/ml | 23 | 7 |

The results are even more dramatic when focusing on all cycles with granulosa lutein cell production of relaxin >800 pg/ml (14% of the cycles had relaxin concentrations in this range) had term pregnancies. Conversely, only 3.5% of cycles with relaxin <200 pg/ml (53% of all cycles had relaxin in this range) had term pregnancies.

TABLE III

| Relaxin (pg/ml) | NonConceptive | Conceptive |
|---|---|---|
| >800 | 0 | 8 |
| 200–800 | 9 | 10 |
| <200 | 23 | 7 |

Tables IV and V show that the results are even more dramatic when considering success rates based not just on obtaining conceptions but on obtaining a term pregnancy.

TABLE IV

| (Same Groups as Table II above) | | |
|---|---|---|
| Relaxin | Non-Term | Term |
| >200 pg/ml | 13 | 14 |
| ≦200 pg/ml | 28 | 2 |

TABLE V

| (Same Groups as Table III above) | | |
|---|---|---|
| Relaxin (pg/ml) | Non-Term | Term |
| >800 | 0 | 8 |
| 200–800 | 13 | 6 |
| <200 | 28 | 2 |

Levels of relaxin can be measured by extracting granulosa cells from the patient along with an in vitro fertilization procedure. The granulosa cells can be cultured in the manner specifically described within Example 58. Cellular extract can be removed each day and relaxin levels or levels of other hormones measured each day with the measured liquid then being discarded. In general, relaxin begins to appear around day 6 or 7 and maximizes at around day 10. Accordingly, it is most desirable to determine the relaxin level at day 10. Further, any of these hormones can be measured in blood serum.

Steroid concentrations of estradiol and progesterone from cultured cells were not predictive of conception. While it has generally been accepted that estrogen and progesterone are sufficient to adequately prepare the endometrium, it is noted that endometrial morphology does not always imply normal endometrial receptivity. The ability of some pregnancies to survive with estradiol and progesterone treatment alone (such as in premature ovarian failure patients) does not preclude other hormonal adjuvants from improving the conception rate in IVF. As the embryo transfer success rate is poor, there may be additional ovarian factors which would optimize conception rates. The data provided here show that additional relaxin improves implantation and pregnancy success rates in IVF/ET.

THEORY OF RELAXIN EFFECT

Without being bound to any particular theory of how or why relaxin might effect a successful pregnancy it is pointed out that there are several means by which lowered circulating relaxin concentrations might influence implantation success. Perhaps the most profound and least studied actions of relaxin on endometrial development may be on the vasculature. Hypertrophy and hyperplasia of endothelium in maternal blood vessels of the uterine endometrium during gestation in monkeys occur in the first month of pregnancy. This reaction can be induced and enhanced in nonpregnant and castrated monkeys by giving estrogen, progesterone and relaxin in proper sequence. Relaxin induces dilation of superficial endometrium blood vessels and proliferation of the endothelial cells. The effects produced seem to be a direct response of the endothelium to relaxin, as they occur only when this hormone is administered.

During the follicular phase in women, spiral arteries have a straight course but in the secretory phase they grow longer, thicker and become spirally twisted. On the 9th day after ovulation, groups of spiral arterioles become prominent. This is closely timed to the increase in relaxin that we have observed in circulation during the luteal phase where relaxin is first detected about day 6–7 and then rapidly increases. Thus luteal endometrial blood vessel development and angiogenesis may be important to the implantation process and success of the pregnancy.

Angiogenesis has been shown to have an essential role in implantation as demonstrated by administration to pregnant mice of an agent which inhibits angiogenesis. Treatment with AGM 1470 O-chloracetyl carbamoyl fumagillol prior to or shortly after implantation prevented all live births while administration at midpregnancy had no effect on fetal survival. Uterine artery blood flow measured on the day of oocyte retrieval as measured by Doppler flow measurements was positively correlated with pregnancy success in IVF. It has also been demonstrated that in women with impaired uterine perfusion the administration of low dose aspirin is associated with improved blood flow and improved pregnancy rates. Spiral artery development is also known to be important for proper implantation as the invasive cytotrophoblast shows preference for maternal vessels in early implantation. Inadequate invasion and remodeling has been associated with pregnancies complicated by hypertension and intrauterine growth retardation and has been suggested as a cause of miscarriages. Deficient invasion of trophoblast cells into the endometrium and failure of the remodeling of the uterine spiral arteries are histopathological hallmarks of preeclampsia.

Another possible mechanism by which relaxin could be involved in aiding a successful implantation is through the stimulation of glycodelin release by the endometrium. Relaxin is a direct stimulus for glycodelin secretion. Glycodelin is a potent immunosuppressive which may be needed to prevent maternal rejection of the embryo. For this reason measuring levels of glycodelin should provide a predictor of IVF/ET success.

Relaxin is highly effective in reducing the amplitude of spontaneous and induced uterine contractions in several species. Endometrial wavelike movement occurs during menstrual cycle and cycles with few waves have a greater conception rate. However, porcine relaxin and synthetic human relaxin have little or only a slight effect on spontaneous contractility of human myometrial tissue. Thus, relaxin may play a minor role in uterine quiescence in the human although it remains to be determined if administered relaxin will cause uterine quiesce in vitro.

GRANULOSA LUTEIN CELL CULTURE (GLCC)

Figure 6:
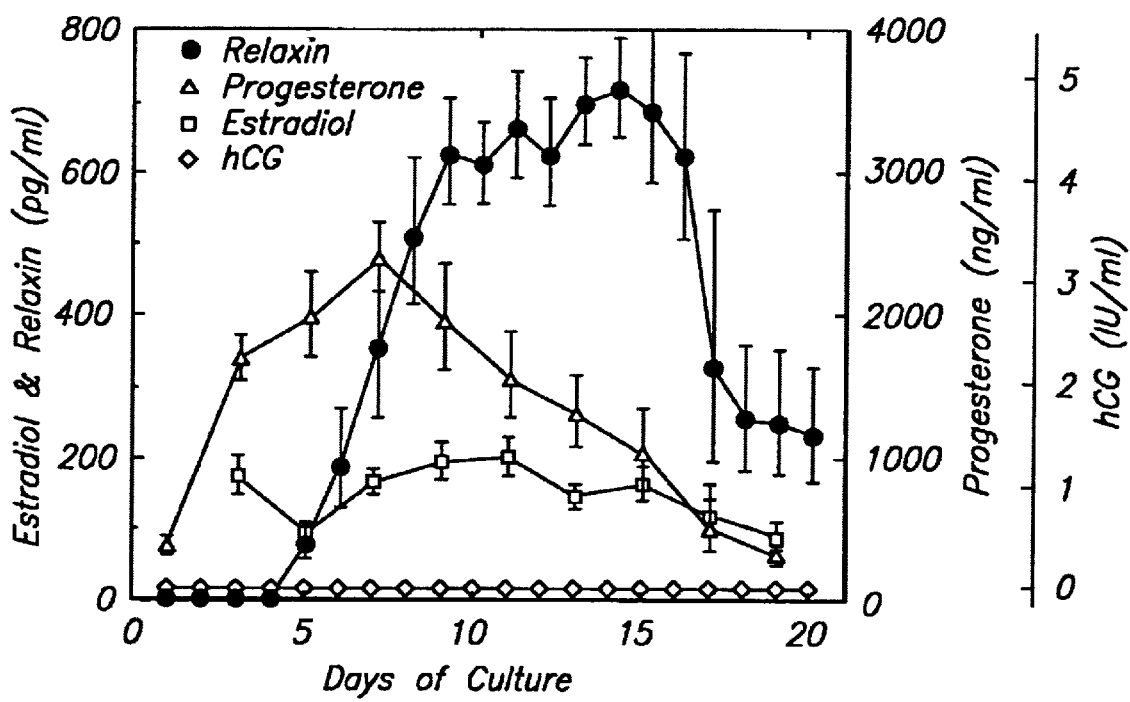
FIG. 6 is a graph showing the average concentration of relaxin (pg/ml) progesterone (ng/ml) estradiol (pg/m) and hCG (IU/ml) over 20 days in ten different cultures of human granulosa cells obtained from ten different human female IVF/ET patients.

Human granulosa cells were obtained from IVF/ET human female patients. The granulosa lutein cell culture (GLCC) was carried out over a period of 20 days. As shown in FIG. 6 the endocrine profiles in terms of concentration closely mimic the in vivo endocrine profiles which are shown within FIG. 7. The GLCC cell culture utilized an extracellular matrix (produced by Matrigel, Collaborative Biomedical) and utilized low doses of hCG (0.02 IU/ml). Thus, the invention includes a GLCC which adds less than 0.5 IU/ml, preferably less than 0.1 IU/ml and most preferably about 0.02 IU/ml. This dosage range of hCG used here is substantially below that previously used in GLCC assays. More specifically, others added 50 times as much hCG or more (generally 500 to 5,000 times more) hCG to the GLCC. This results in increasing the relaxin level inappropriately relative to the relaxin level in serum.

Figure 7:
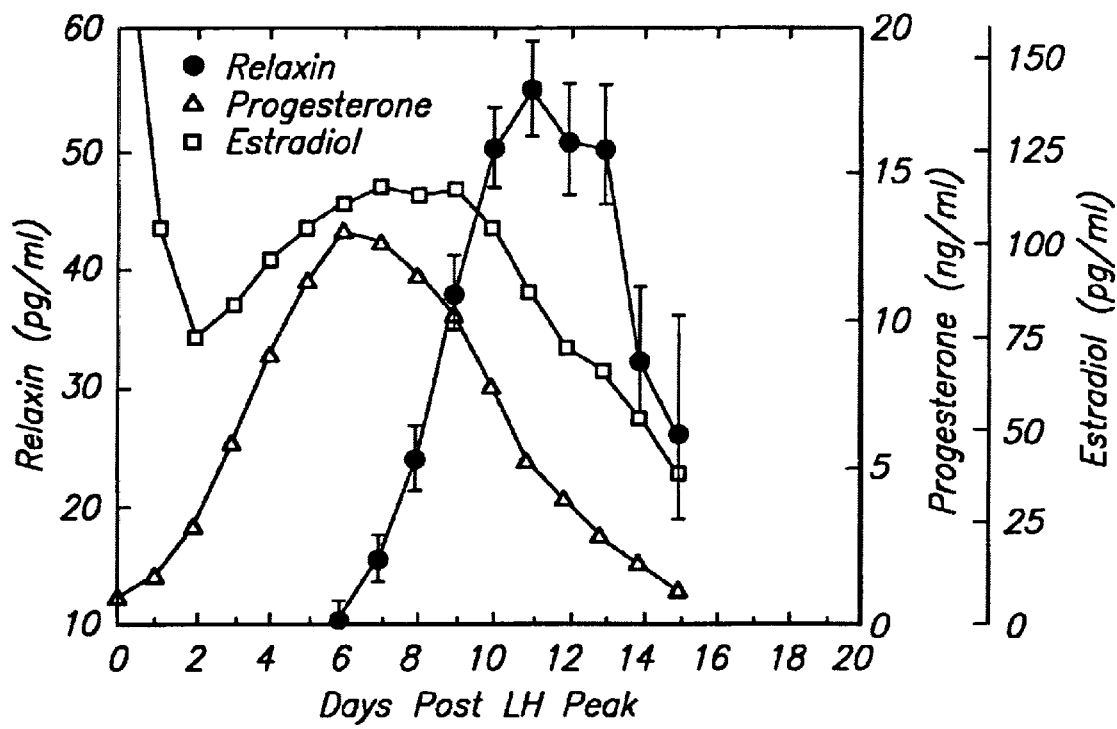
FIG. 7 is a graph showing the average concentration of relaxin (pg/m) progesterone (ng/ml) and estradiol (pg/ml) over 20 days in vivo for over 100 human female patients.

The data shown within FIGS. 6 and 7 indicates that in vitro relaxin secretion is timely with in vivo secretion as relaxin becomes detectable in serum at about 6 to 8 days following the LH peak. The granulosa cells are aspirated for 36 hours after the administration of the hCG dose in order to stimulate the LH surge which occurs naturally in vivo. Therefore, the "days in culture" are approximately 1 and ½ days skewed (advanced) over "days post LH peak" of in vivo luteal cells. Thus, for example, a 5 day GLCC culture corresponds approximately to a 6 and ½ day post LH peak in vivo.

As shown within FIGS. 6 and 7 the GLCC system provides profiles with respect to estradiol, progesterone and relaxin that are remarkably similar to those seen in vivo-compare FIGS. 6 and 7. It is particularly important to note that these secretory profiles are independent of changing gonadotropin indicating that these profiles represent endogenous patterns of secretion. The GLCC system also reflects the decline in ovarian steroids and relaxin seen in circulation. The decline occurs in the face of continuous baseline hCG concentrations. The decline in relaxin secretion as shown here has not previously been seen in other GLCC assays which utilize the higher hCG stimulation that maintains cells maximally stimulated. The culture system utilized here provides a unique ability to study in vitro the mechanisms of control of relaxin secretion in a manner which is relevant to the in vivo cycle.

GLCC ENDOCRINE RESPONSES: NON-RESPONDERS VERSUS RESPONDERS

Figure 8:
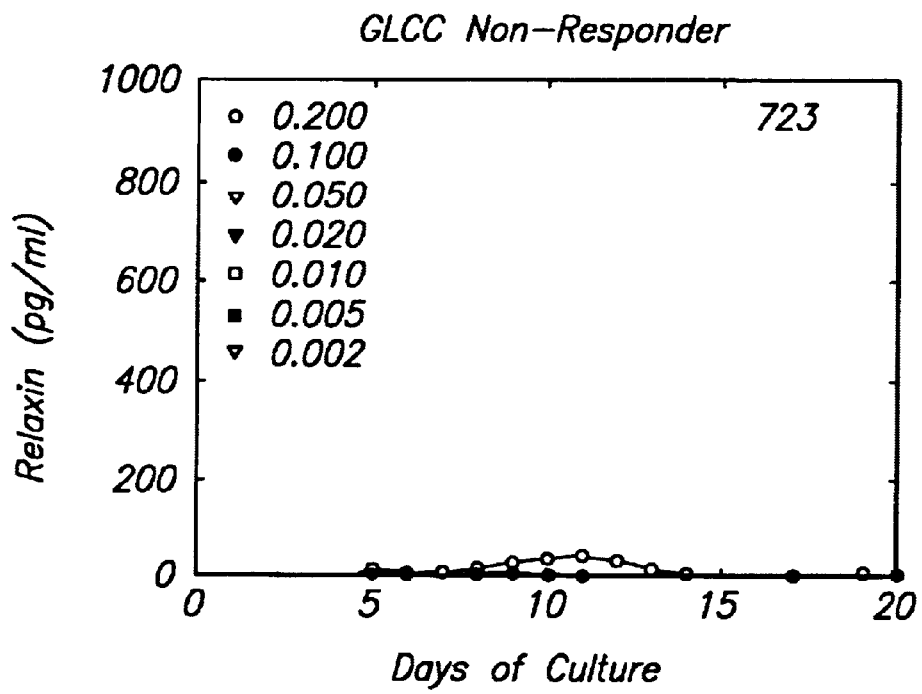
FIG. 8 is a graph showing the concentration of relaxin (pg/ml) over twenty days in a Granulosa Latein Cell Culture (GLCC) for a single "non-responder" given different doses of hCG.
Figure 9:
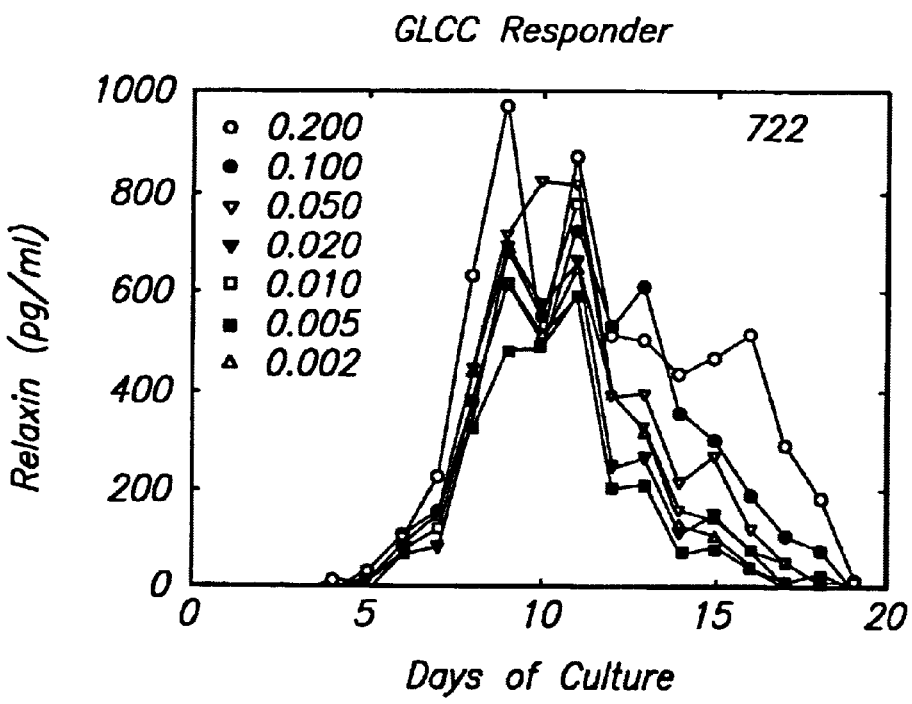
FIG. 9 is a graph showing the concentration of relaxin (pg/ml) over twenty days in a Granulosa Latein Cell Culture (GLCC) for a single "responder" given different doses of hCG.

FIGS. 8 and 9 include data comparing a non-responder with a responder given different doses of hCG to determine if additional hCG would turn a non-responder into a responder. The different lines in each graph are for the different doses of hCG. The data clearly shows that there is a wide range in the amount of hormones secreted by GLCC from different patients, especially in terms of the amount of relaxin. The terms "responder" and "non-responder" are terms which refer to results obtained based on the amount of relaxin secreted. The term provides an arbitrary distinction even though there appears to be a continuum in terms of relaxin secretion. The responders are defined as GLCC with a 10 day relaxin concentration greater than 200 pg/ml at an hCG dose of 0.02 IU/ml. While the cells from some patients may have a relaxin concentration of >200 pg/ml on day 10 at doses of hCG >0.020 IU/ml, they would still be considered non-responders because the relaxin concentration is <200 pg/ml for that produced by the 0.02 IU/ml of hCG.

A culture system of a more conventional type which generally used around 100 IU/ml hCG would be unable to identify non-responders as defined here. It should be noted that ovarian steroids are also reduced in the non-responders but not to the same magnitude shown with respect to the relaxin concentration.

GLCC RELAXIN PRODUCTION AS A PREDICTOR OF PREGNANCY SUCCESS

Figure 5:
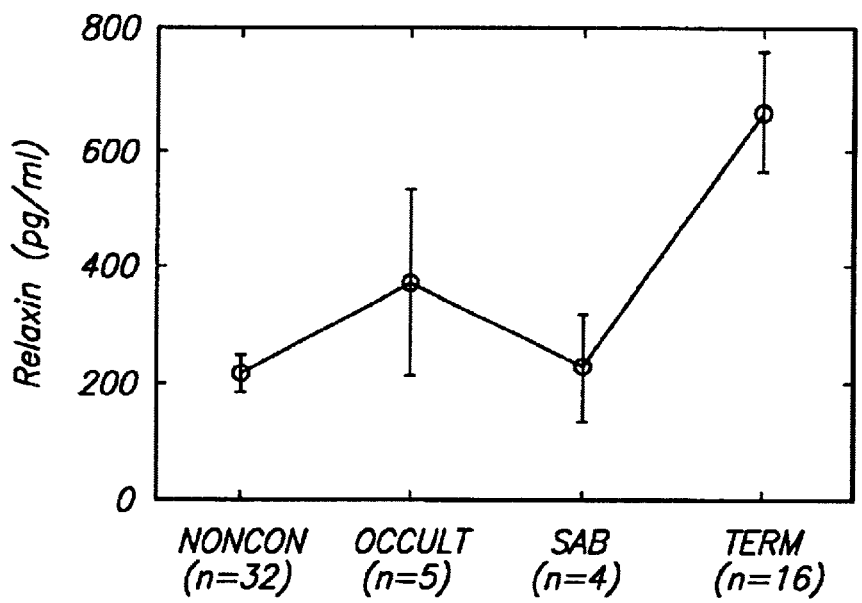
FIG. 5 is a graph showing the mean relaxin concentration of all patients in the group on day 10 of cultured granulosa cells with the patients grouped by (a) no conception; (b) occult; (c) spontaneous abortion; and (d) term deliveries.

The 10 day GLCC relaxin concentrations are predictive of both conception success (see FIG. 1) and pregnancy outcome (see FIGS. 2 and 5). There are certain factors other than relaxin which are required for conception so that the fact that 9 of 27 cycles with the relaxin concentration >200 pg/ml did not conceive is not surprising. However, it is remarkable that only 2 of 30 cycles with relaxin concentrations <200 resulted in a full term pregnancy. These data indicate that it is necessary for the granulosis cells to produce relaxin at an effective level in order to obtain successful gestation.

The predictive effect of GLCC hormone production appears to be predictive when considering the relaxin concentration but not when considering the concentration of other ovarian steroids . Neither estradiol or progesterone concentration on day 11 of GLCC are significantly different between nonconceptive and successful pregnancy cycles. However, the day 10 relaxin secretion is significantly higher from cycles which have a successful pregnancy as compared with the day 10 relaxin concentration from nonconceptive cycles. These data indicate that relaxin is predictive of pregnancy success and also provides evidence that relaxin is necessary in order to obtain a successful full term pregnancy.

RELAXIN PRODUCTION IN CULTURE VERSUS CIRCULATING RELAXIN CONCENTRATION

Figure 10A:
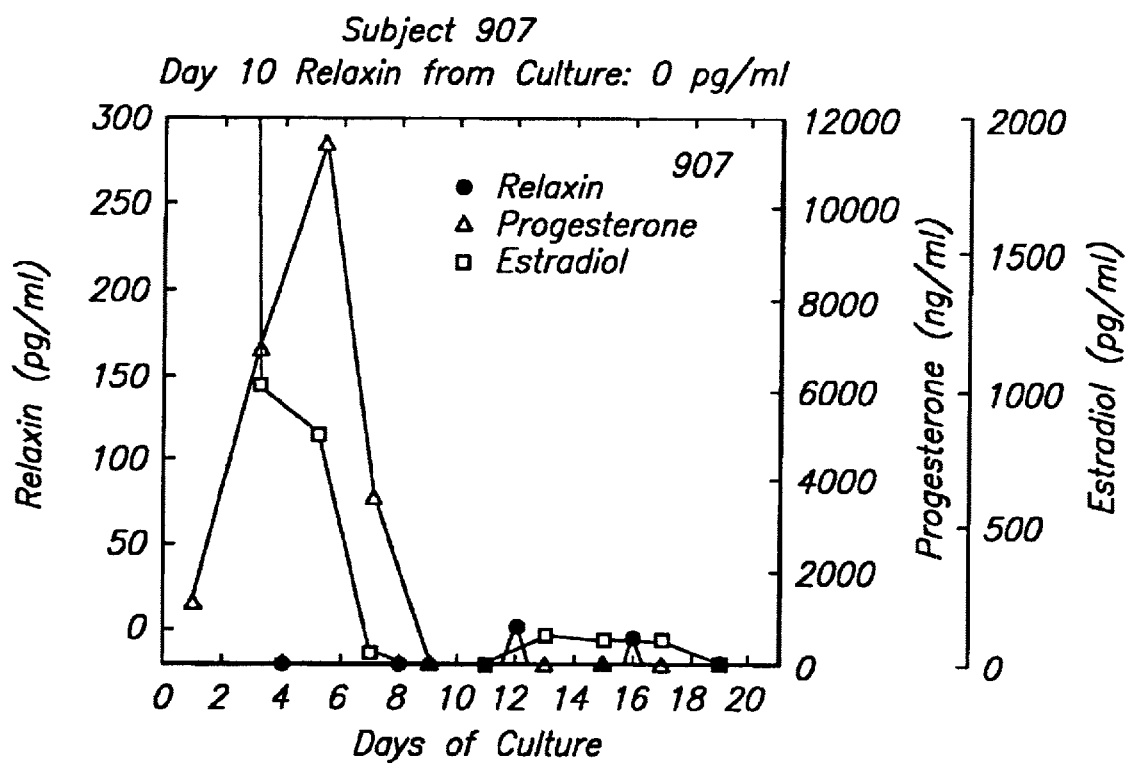
FIG. 10A is a graph showing the concentration of relaxin (pg/ml), progesterone (ng/ml) and estradiol (pg/ml) over 18 days for an in vitro cell culture of cells extracted from a single individual.
Figure 10B:
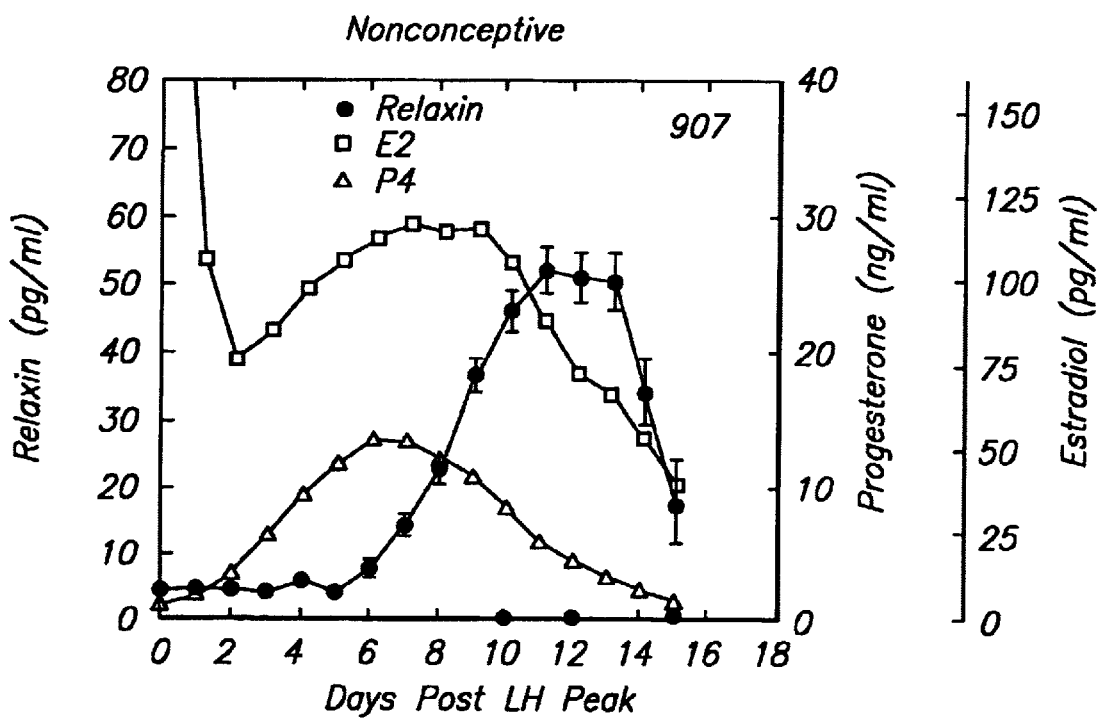
FIG. 10B is a graph showing results from the same patient plotted in FIG. 10A but with the data being derived from serum extracted from the same individual (at the same time) as that of FIG. 11A. The cycle of FIGS. 10A and 10B is the same nonconceptive cycle.

FIGS. 10A and 10B can be compared in order to show the concentration of relaxin, progesterone and extradiol over the same period of time with FIG. 10A being the concentrations taken from a cell culture and FIG. 10B being the concentrations determined from serum. In both FIGS. 10A and 10B the amount of relaxin is substantially undetectable within the GLCC and also substantially undetectable with the patient's serum. The level of relaxin measured here is substantially lower than normal and this information was extracted from the same individual at the same time, i.e. the same nonconceptive cycle.

Figure 11A:
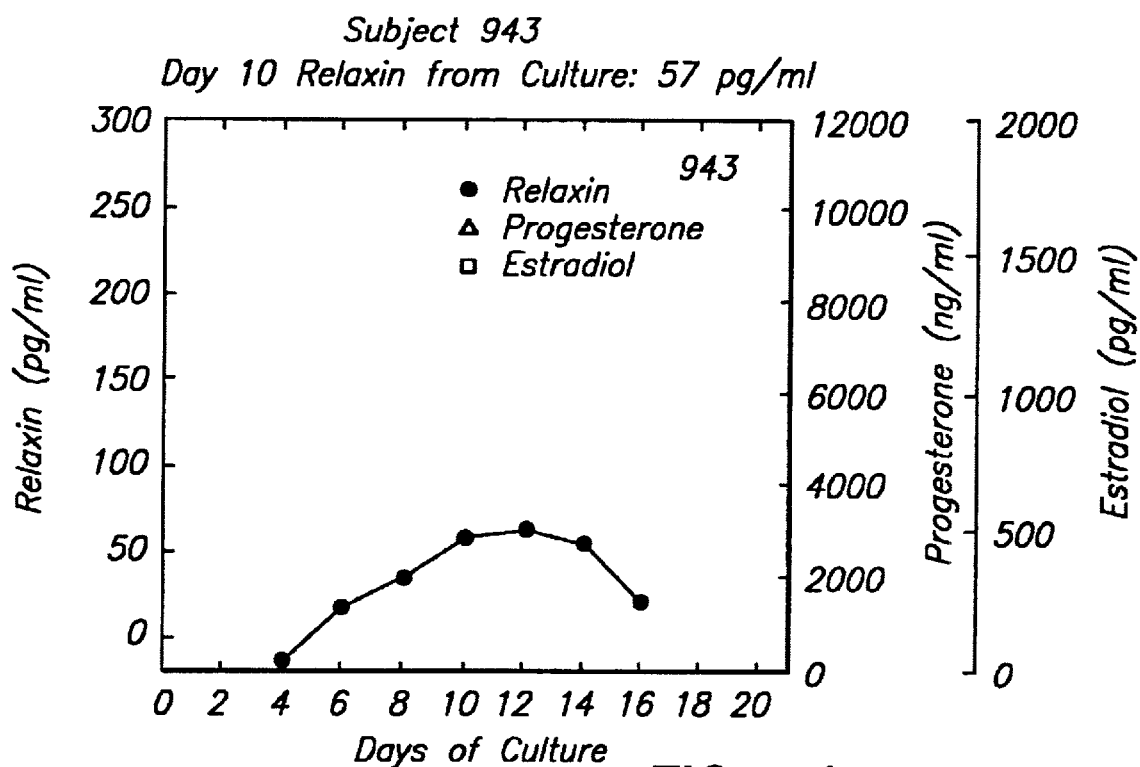
FIG. 11A is a graph showing the concentration of relaxin (pg/ml), progesterone (ng/ml) and estradiol (pg/ml) over 18 days for an in vitro cell culture of cells extracted from a single individual.
Figure 11B:
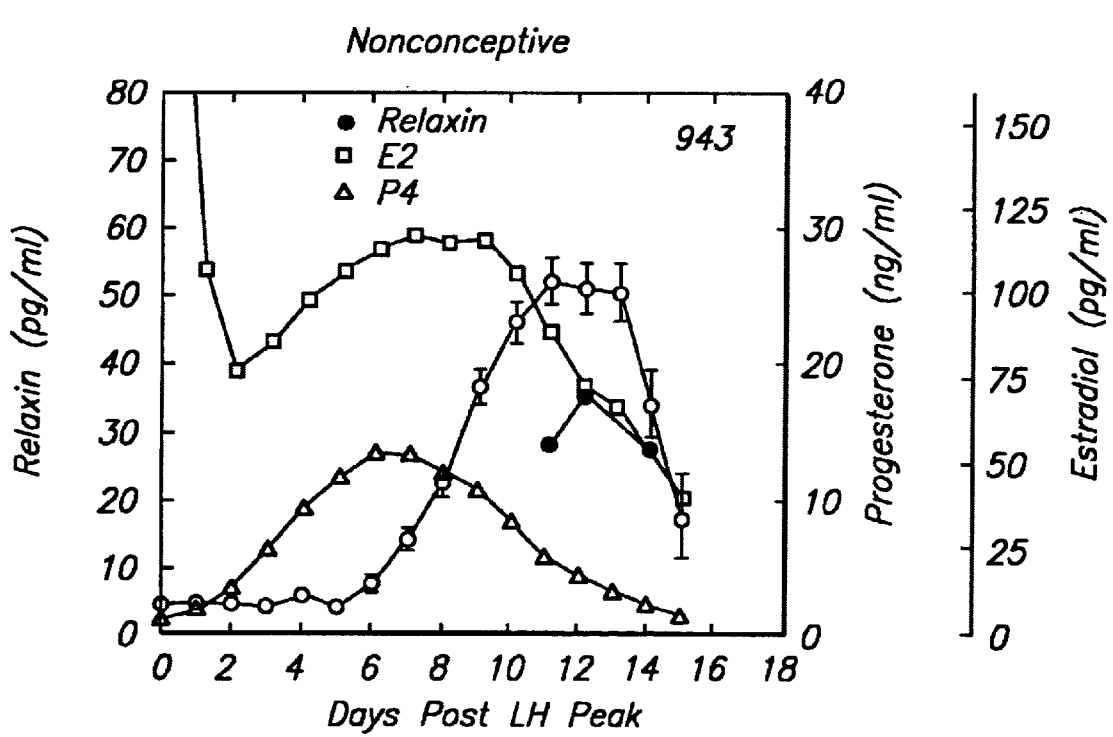
FIG. 11B is a graph showing results from the same patient plotted in FIG. 11A but with the data being derived from serum extracted from the same individual (at the same time) as that of FIG. 11A. The cycle of FIGS. 11A and 11B is the same nonconceptive cycle.

FIGS. 11A and 11B are similar to FIGS. 10A and 10B. FIG. 11A shows the concentration of relaxin, progesterone and estradiol in GLCC. FIG. 11B shows the concentration of the same proteins in the same patient's serum over the same time. The relaxin level in both the cell culture and in serum is less than normal. However, both the cell culture and the serum appear to indicate levels which are above zero but less than normal. This information was extracted from the same individual undergoing a nonconceptive cycle.

Figure 12A:
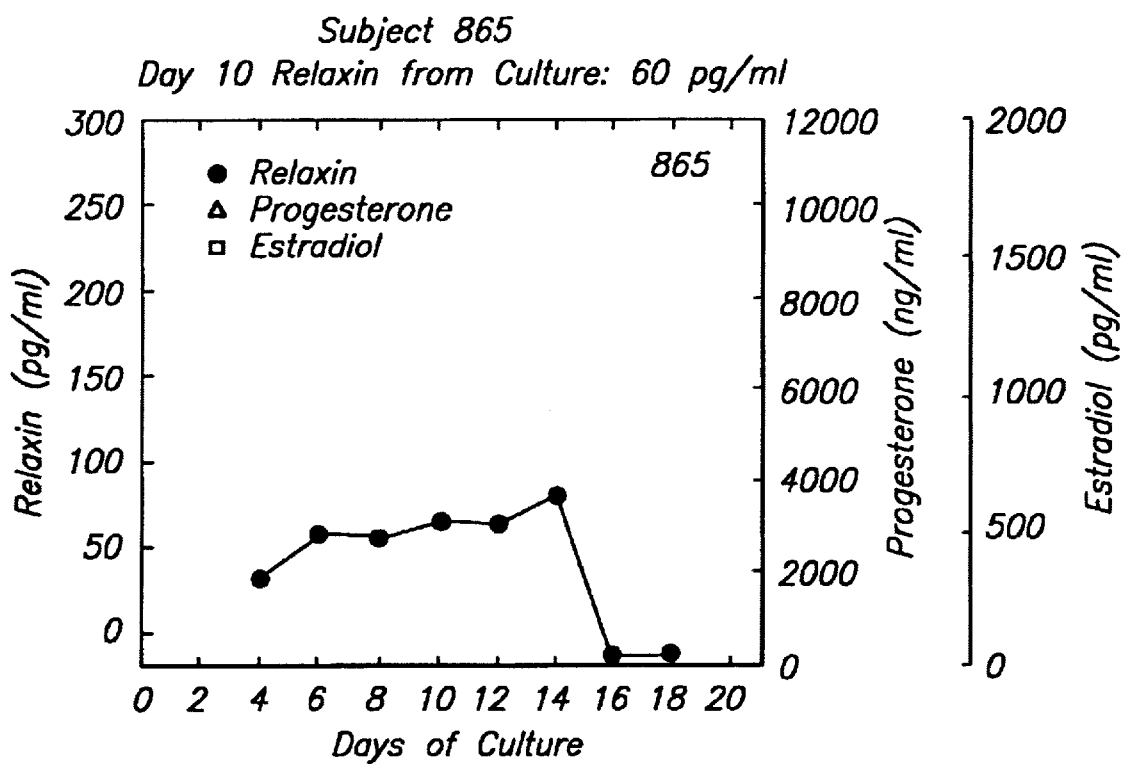
FIG. 12A is a graph showing the concentration of relaxin (pg/ml), progesterone (ng/ml) and estradiol (pg/ml) over 18 days for an in vitro cell culture of cells extracted from a single individual.
Figure 12B:
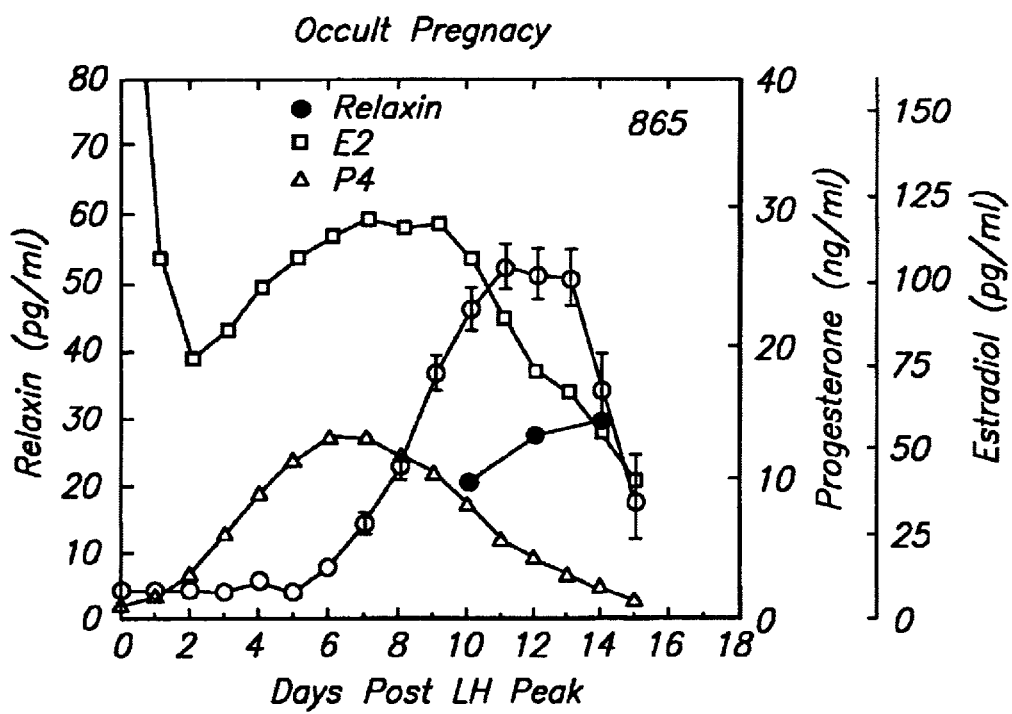
FIG. 12B is a graph showing results from the same patient plotted in FIG. 12A but with the data being derived from serum extracted from the same individual (at the same time) as that of FIG. 12A. The cycle of FIGS. 12A and 12B is the same nonconceptive cycle.

FIGS. 12A and 12B are similar to FIGS. 11A and 11B. However, in FIG. 12A only the relaxin concentration is plotted. Using the culture data and the serum data of FIGS. 12A and 12B it can be seen that the patient is producing some relaxin. This data was obtained from the same woman during the same cycle which was a conceptive cycle, i.e. the woman became pregnant. However, the pregnancy was an occult pregnancy, i.e. the fetus was lost shortly after conception.

The data show that patient's with low relaxin production in culture have abnormally low relaxin in circulation. This endocrine deficiency is not compensated for by a feedback mechanism. This demonstrates that a low circulating relaxin concentration as being responsible for failure to conceive or reach a full term pregnancy. A comparation of FIGS. 10, 11 and 12 shows that when the relaxin level is not detectable in GLCC, it is not detectable in serum and that when it is present at detectable levels in GLCC, it is also present in detectable levels in serum. These results were obtained in GLCC using about 0.2 IU/ml of hCG.

SERUM RELAXIN CONCENTRATIONS IN IVF CYCLES

Figure 13:
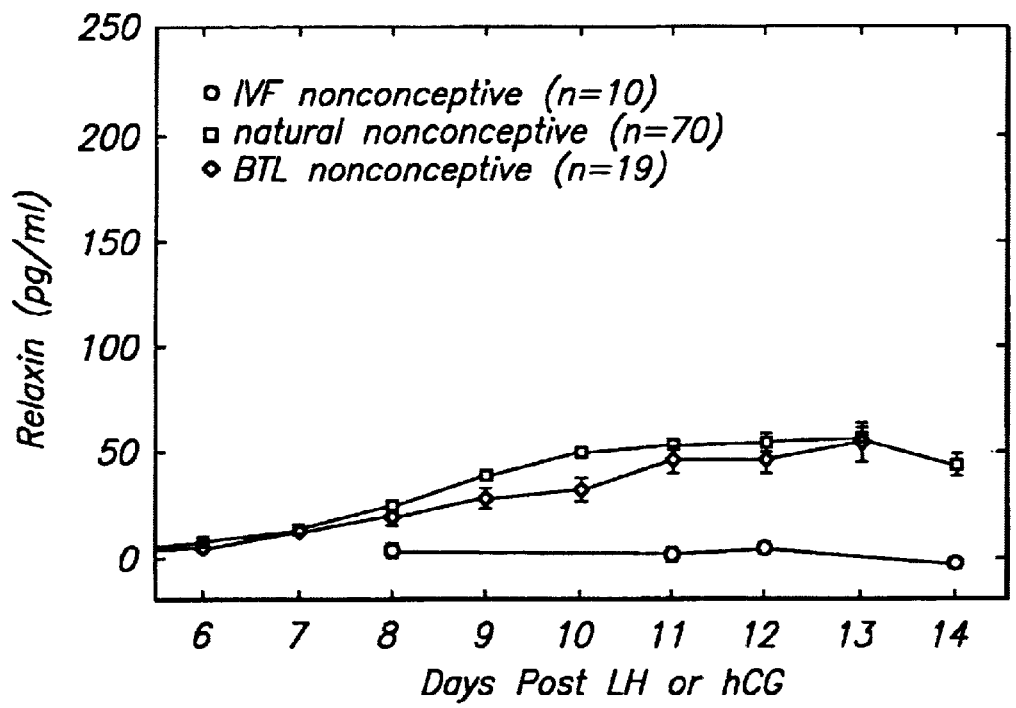
FIG. 13 is a graph showing relaxin (pg/ml) concentration over days 6–14 after LH or hCG administration in vivo for IVF non-conceptive, natural nonconceptive and BTL nonconceptive patients.
Figure 14:
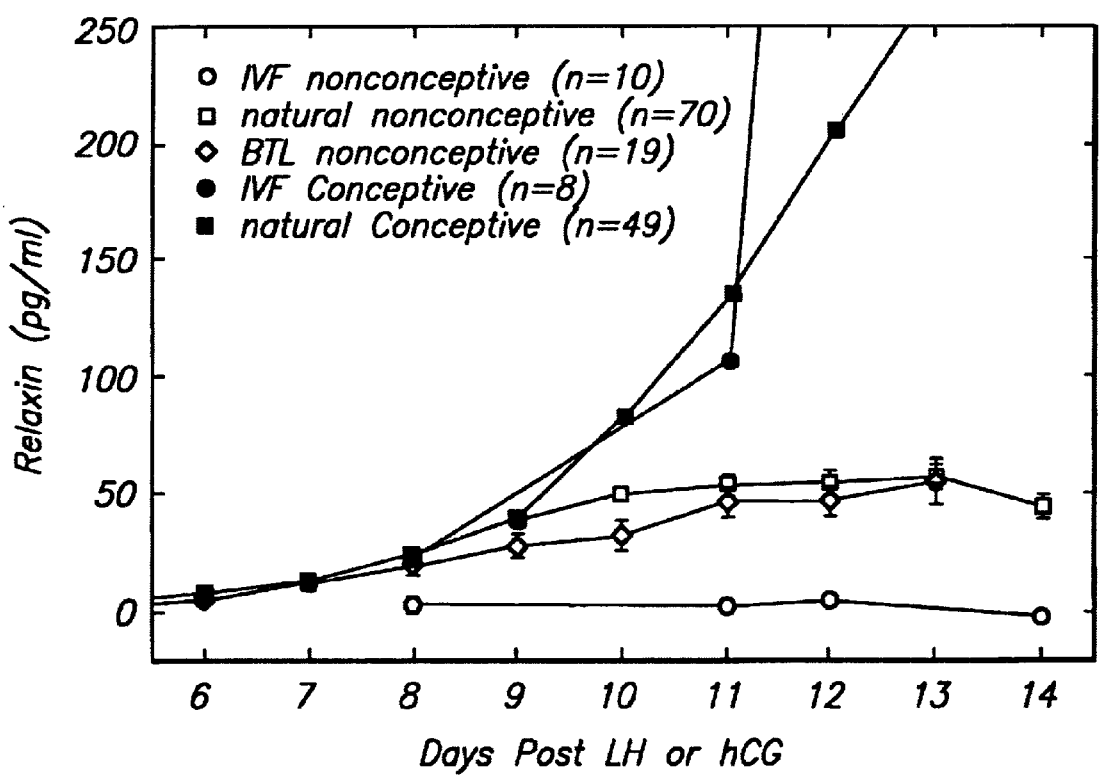
FIG. 14 is a graph showing the data of FIG. 13 along with the relaxin concentration in vivo for IVF conceptive and natural conceptive patients.

Data shown within FIGS. 13 and 14 is data taken from a series of IVF patients which demonstrate that relaxin is abnormally low in non-conceptive cycles from IVF patients. The serums were collected in the luteal phase of women undergoing standard IVF/ET protocols. The cycles were grouped by whether or not a pregnancy occurred.

As shown within FIG. 13, the serum in relaxin in IVF non-conceptive cycles are significantly lower than in "normal" non-conceptive cycles. The data show that relaxin remains extremely low throughout the luteal phase compared with non-conceptive natural cycles. Natural cycles means that there were no exogenous hormones given as is done with IVF patients and represents the natural condition. Bilateral tubal ligation patients were used because they have an extremely low chance of conception and thus represent relaxin levels when conception cannot occur. FIG. 14 shows that IVF patients with conceptive cycles have "normal" amounts of relaxin. These data indicate that IVF cycles form two groups based on their relaxin. There are cycles with abnormally low relaxin and these are the cycles that do not result in pregnancy. However, the IVF cycles with normal relaxin levels are the cycles which result in pregnancy.

It is pointed out that the key differences seen on day 8 after the LH surge or hCG administration. This is prior to when endogenous hCG from the implanting trophoblast stimulates additional relaxin. If relaxin is low on day 8 of the IVF cycle, the cycle is unlikely to result in a pregnancy. If relaxin is "normal" on day 8 of the IVF cycle, it will result in a conception. This is the first indication that serum relaxin is significantly lowered in IVF non-conceptive cycles. The data indicate that the IVF procedure causes some cycles to have abnormally low relaxin and that these cycles do not result in obtaining a pregnancy.

The data shown in FIGS. 13 and 14 indicate that alterations of the conventional or standard IVF protocol which (increase relaxin levels) achieve "normal" relaxin levels would result in the same effect as relaxin administration, and this effect would be to substantially increase the percentage of IVF/ET procedures ultimately resulting in a pregnancy. It may be that premature administration of hCG to IVF patients in a conventional IVF/ET procedure creates "immature" granulosa cells and that these cells do not produce sufficient concentrations of relaxin. Accordingly, waiting until the granulosa cells are fully mature before administering hCG in order to obtain "normal" granulosa cells which produce normal concentrations of relaxin would increase the chance of a successful IVF/ET procedure, i.e., increase the probability of ultimately obtaining a pregnancy.

EFFECTS OF CIRCULATING RELAXIN ON THE ENDOMETRIUM

Figure 15:
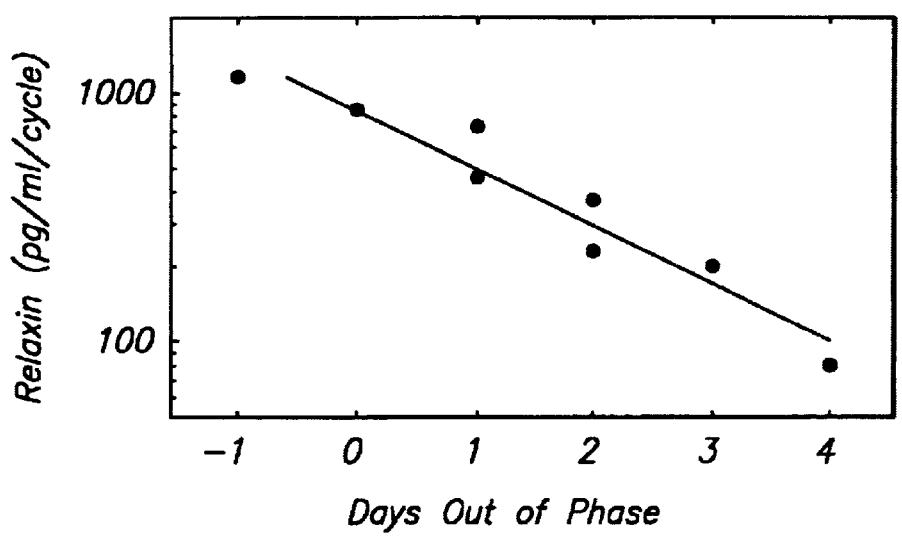
FIG. 15 is a graph showing relaxin concentration versus days out of phase on the endometrial biopsies.

Data plotted within FIG. 15 show that circulating relaxin is lower than normal in menstrual cycles with out-of-phase endometrial biopsies. These data plotted in the graph of FIG.

15 show the relation of days out-of-phase to the total luteal phase relaxin during the cycle, indicating an association of low circulating relaxin with an underdeveloped endometrium. The relationship of the relaxin concentration to endometrial development is substantially stronger than that of progesterone and the stage of the endometrium. The data suggest that relaxin aids the development of a normal endometrium.

Figure 16:
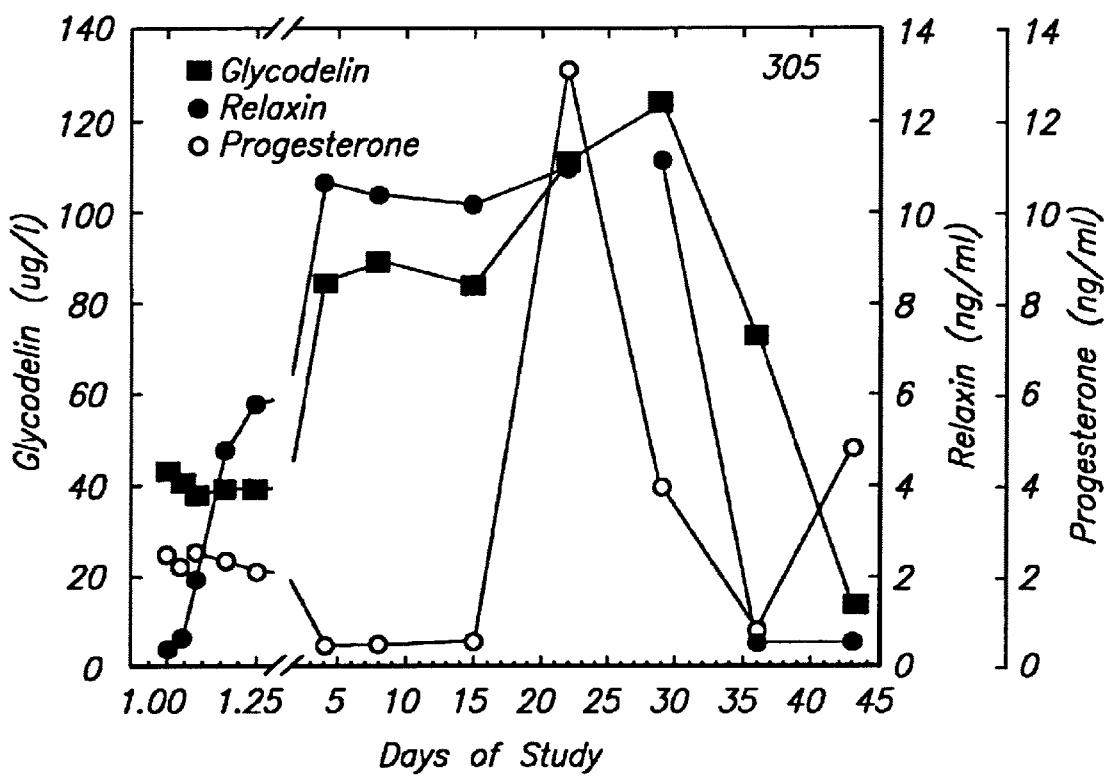
FIG. 16 is a graph showing the concentration of glycodelin secretion ($\mu$g/l) in response to administration of relaxin-progesterone concentration also shown.

The data plotted with FIG. 16 show that relaxin is involved in the control of glycodelin secretion from the uterine granular tissues. Glycodelin is a glycoprotein associated with the suppression of the immune response in the endometrium and thus may be important in order to prevent fetal rejection. The data plotted in FIG. 16 demonstrates the secretion of glycodelin in response to relaxin administration. A close temporal relationship between relaxin and glycodelin secretion in the late luteal phase and early pregnancy exists but is not shown in the figures. The data also demonstrate that the administration of relaxin would cause glycodelin secretion, even at times of the cycle when it is not normally secreted (see FIG. 16). Thus, the data of FIGS. 15 and 16 demonstrate that relaxin effects both endometrial morphology and function respectively and thus plays a role in preparing the endometrium for implantation.

DATA ON CIRCULATING RELAXIN AND ENDOMETRIAL DEVELOPMENT

Figure 17:
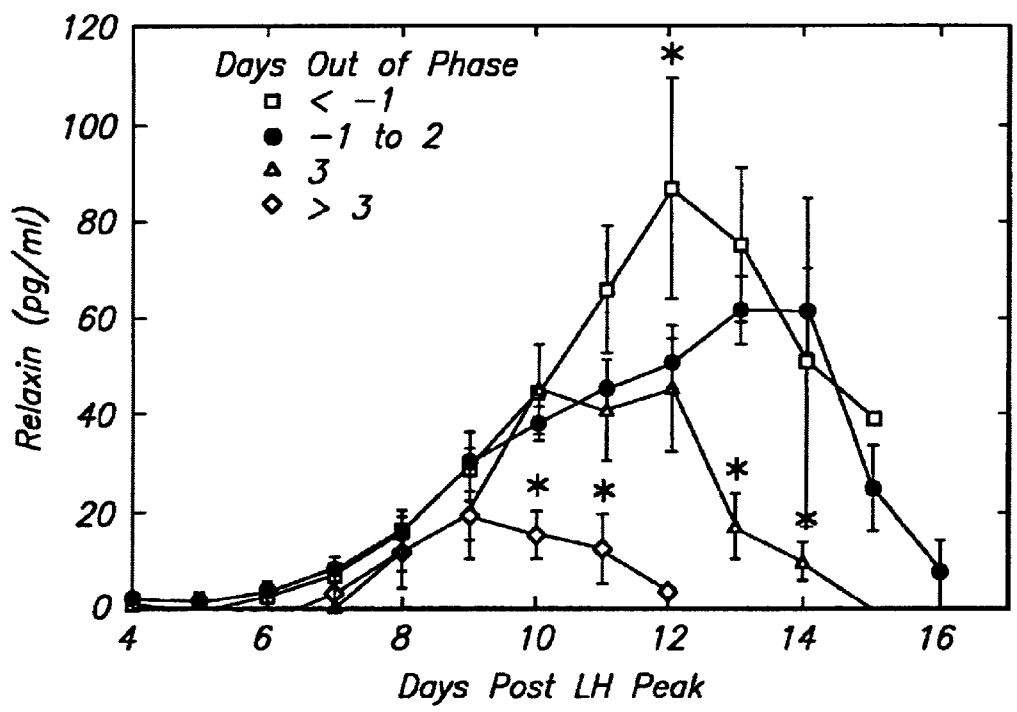
FIG. 17 is a graph showing the concentration of relaxin (pg/ml) over a period of from 4 to 16 days after peak levels of LH, in vivo for four different groups of women grouped based on their endometrial biopsy.

Data plotted within FIG. 17 show the mean serum relaxin in women grouped by the dating of their endometrial biopsy. Women with advanced biopsies (<-1) had higher than normal relaxin concentrations. Women with biopsies showing retarded development had lower circulating relaxin. Thus, the data plotted within FIG. 17 shows the same concept demonstrated within the data of FIGS. 15 and 16 but with a greater number of women. The combined data shown here indicate that relaxin would be useful in the treatment of a large group of infertile women and not be limited simply to improving the percentage rate of conception and full term pregnancy for women undergoing IVF/ET procedures.

DOSAGE AND ADMINISTRATION

Relaxin is administered at a therapeutically effective dosage, e.g., a dosage sufficient to treat infertility and improve the chance of successful term pregnancy.

Administration of relaxin can be via any of the accepted modes of administration for agents that serve similar utilities, preferably by systemic administration.

While human dosage levels for treating infertility have yet to be optimized for relaxin, generally, a daily dose is from about 0.1 to 500.0 µg/kg of body weight per day, preferably about 6.0 to 200.0 µg/kg, and most preferably about 12.0 to 100.0 µg/kg. Generally it is sought to obtain a serum concentration of relaxin approximating or greater than normal circulating levels in pregnancy, i.e., 1.0 ng/ml, such as 0.5 to 50 ng/ml, preferably 1.0 to 20 ng/ml. For administration to a 70 kg person, the dosage range would be about 7.0 µg to 3.5 mg per day, preferably about 42.0 µg to 2.1 mg per day, and most preferably about 84.0 to 700.0 µg per day. The amount of relaxin administered will, of course, be dependent on the subject and the severity of the affliction, the manner and schedule of administration and the judgment of the prescribing physician. The data presented here show that individual women vary greatly in terms of relaxin concentration. Thus, the relaxin level of the woman being treated should be determined prior to determining dosage.

In employing relaxin for treatment of infertility, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and relaxin. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of relaxin, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The formulations of human relaxin described in U.S. Pat. No. 5,451,572, issued Sep. 19, 1995, incorporated herein by reference, are particularly preferred.

Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the relaxin in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, U.S. Pat. Nos. 3,845,770 (describing elementary osmotic pumps); 3,995,651, 4,034,756 and 4,111,202 (describing miniature osmotic pumps); 4,320,759 and 4,449,983 (describing multichamber osmotic systems referred to as push-pull and push-melt osmotic pumps); and 5,023,088 (describing osmotic pumps patterned for the sequentially timed dispensing of various dosage units).

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of relaxin in the present invention.

ENHANCING ENDOGENOUS RELAXIN PRODUCTION

Standard IVF/ET protocols have been established. However, these protocols do not consider factors which effect relaxin levels. Further, these protocols, which include administration of hCG, are based on aggregate estrogen production by a number of follicles. Thus, the estrogen level is more reflective of the number of growing follicles rather than the maturity of a single dominant follicle as in a nature cycle. Accordingly, hCG stimulation, pursuant to conventional IVF/ET protocols, occurs before the leading follicle has properly matured. This forces conversion to luteal cells prior to full granulosa cell development resulting in low relaxin concentrations in culture, i.e., resulting in nonresponders.

In accordance with the present invention it is possible to enhance the success rate of IVF/ET procedures by modifying the conventional IVF/ET protocol in a manner which results in the patient's indigenous relaxin level being increased. One measure of the maturity of the leading follicles is the progesterone production at the time of hCG stimulation. Progesterone indicates the maturity of the granulosa cells and has been shown to predict pregnancy success. Accordingly, one specific means of modifying standard IVF/ET protocols is to measure progesterone production (preferably on a daily basis) and to administer hCG at a point related to a noted increase in progesterone production.

Because the standard protocol HVF/ET treatments is based on estrogen levels resulting from a number of growing follicles rather than a single dominant follicle the progesterone level readings are skewed. More specifically, the hCG administration (in a conventional IVF/ET procedure) is premature in that the cycle has not been allowed to proceed for a sufficient amount of time after a noted estrogen rise, thereby resulting in immature granulosa cells at the point of hCG stimulation. This inaccuracy can be accounted for by delaying the point of hCG administration for a period of time beyond that at which the administration would occur during the normal HVF/ET protocol. Specifically, it would be desirable to delay the administration for approximately 0.5 to 2.5 days after the point in which the hCG administration would occur pursuant to the normal IVF/ET protocol.

In natural cycles, feedback controls optimize the timing and the nature of the LH surge. However, during IVF/ET cycles the pharmacological stimulation with hCG is based on an aggregate estrogen production by a number of follicles each of which may be at different stages of development. Accordingly, pursuant to the standard IVF/ET procedure the hCG stimulation is not well synchronized with the maturity of the leading follicle but rather, is synchronized based on an average of number of follicles. Cells which are luteinized prior to full maturity never acquire the ability to secrete normal amounts of relaxin during the luteal phase. Accordingly, if none of the follicles are sufficiently mature the luteal phase will occur with undetectable amounts of relaxin. Granulosa cells are known to begin the secretions of small amounts of progesterone just prior to the LH surge in natural cycles and progesterone secretion at the time of hCG stimulation has been used as an indication of follicular maturity.

Based on the above it can be seen that one aspect of the invention is a method of enhancing the probability of obtaining a successful in vitro fertilization or embryo transfer procedure by manipulating the parameters of the conventional procedure in order to increase the endogenous levels of relaxin. This may be carried out by varying the time within the patient's cycle when hCG is administered to the patient and, most likely be varying that time so that it is somewhat later than normal and later by an amount in the range of about 0.5 to 2.5 days compared to the time when hCG is normally administered. More preferably, the point of administration of hCG is based on the point of progesterone increase as noted by close monitoring on a daily basis or more frequent basis as compared to conventional IVF/ET protocols. Those skilled in the art will recognize that other modification may also be useful in enhancing the level of endogenous relaxin and thereby enhancing the probability of attaining a successful IVF/ET procedure.

EXAMPLES

The following examples are put forth so as to provide those of ordinary skill in the art with a complete disclosure and description of how to make and use the assays and methods of the present invention, and are not intended to limit the scope of what the inventors regard as their invention, nor are they intended to represent or imply that the results and experiments below are all of or the only results obtained or experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

EXAMPLES 1–57

Fifty-seven human female patients ranging in age of from 26 to 44 (age not determined in eight patients) were assayed to determine the level of relaxin. Granulosa cells (GCs) were extracted from each patient as part of IVF/ET procedures. When the amount of relaxin produced by granulosa lutein cell cultures (n=57) was grouped by cycle outcome, either nonconceptive or conceptive, it was found that the mean for nonconceptives was lower than for conceptives (FIG. 1). The methods and materials used in the Examples are described in a separate section below and the details of the assay produced are provided in Example 58.

The results for the 57 patients were divided into those less than or equal to 200 pg/ml on day 10 of culture as shown in Table II. The cultures could also be divided into three groups: <200 pg/ml, and >800 pg/ml as shown in Table III. This also resulted in a significant association of relaxin and conception success.

The conceptive cycles could be subdivided into occults (short term gestation) spontaneous abortions (SABs after longer term pregnancies), and termgestations (FIG. 2). This data could be tabled into term pregnancies and non-term cycles which consisted of nonconceptive cycles, occults and SABs (Table IV). There was a positive association of relaxin concentrations with term pregnancy. Using the criteria of three levels of relaxin secretion also resulted in a positive association of relaxin concentrations and a successful gestation (Table V).

A comparison of mean levels of estradiol or progesterone did not show a significant difference between levels from nonconceptive cycles vs term cycles (FIGS. 3 and 4). Relaxin was the only hormone of the three measured that showed a significant difference between nonconceptive and conceptive cycles (FIGS. 3, 4 and 5). More specifically, the estrogen (E2) and progesterone (P4) levels of the granulosa cells were also measured and shown to not be directly related to a likelihood of a successful and/or unsuccessful pregnancy.

Details for the methods and materials used to obtain these results are provided below.

MATERIALS AND METHODS

Culture Conditions

Culture conditions were those described in Stewart, et al., J. Clin. Endo. Metabol. (1997). Briefly, extracellular matrix was applied to culture dishes on the same day cells were collected according to the manufacturer's directions. Minimal Essential Medium (MEM, Gibco, Grand Island, N.Y.) is modified with the following additions: sodium bicarbonate, 4.4 mg/100 ml MEM (Sigma), fungizone, 1 ml/100 ml (Gibco); penicillin G, 6 mg/100 ml (Sigma); streptomycin sulfate, 6 mg/100 ml (Sigma) and 10% fetal calf serum (Hyclone, Logan, Utah). Media is filtered through a 0.22 micron sterile syringe filter (Fisher, Santa Clara, Calif.) and equilibrated at 37 C. and 5% $CO_2$ in air prior to use. hCG (Pregnyl, Organon, W. Orange, N.J.) was added to the culture media in amounts as described below.

Cell Collection

Human granulosa cells (GCs) were obtained by ultrasound-guided follicle aspiration from women receiving assisted reproduction treatment at Pacific Fertility Center (Sacramento, Calif.). The cells were a by-product of the IVF/ET procedure and are normally discarded. They were provided as coded samples with the identities of the women unavailable.

The patients received varying doses of Metrodin (Serono) and Progonal (Serono) and received 10,000 IU of hCG 36 hrs prior to folicular aspiration. Approximately 1.0 ml modified human Tubal Fluid Media (Irvine Scientific, Santa Ana, Calif.) containing HEPES buffer, antibiotics, and heparin, was added to the follicular fluid during the oocyte retrieval procedure. After oocytes and cumulus masses were removed, the follicular fluid containing granulosa cells was refrigerated and transported on ice to California Regional Primate Research Center in a 50 ml flask. Individual follicles were not distinguished as all granulosa cells from an individual were pooled. Cells from different subjects were not pooled.

Assays

Estradiol and progesterone were measured by commercial kits (Diagnostics Products Corp., Los Angeles, Calif.) as described in Stewart, et al., J. Clin. Endo. Metab. 76:1470–1476 (1993). Relaxin was measured by an enzyme immunoassay as in the manner which serum relaxin was measured in Stewart, et al., J. Clin. Endo. Metab. 7-:1771-3 (1990). The assay was modified by dilution of human relaxin using culture fluid instead of human serum for preparation of standards.

Data Analysis

To normalize the endocrine data, the values were converted to the common logarithm for statistical analysis and averaging. Data were converted to arithmetic scale for graphing (geometric mean).

EXAMPLE 58

CORRELATION OF RELAXIN CONCENTRATION AND IVF/ET SUCCESS

Media and Plate Preparation

Minimal Essential Medium (MEM, Gibco, Grand Island, N.Y.) is modified with the following additions: sodium bicarbonate, 4.4 mg / 100 ml MEM (Sigma); fungizone, 1 ml/ 100 ml (Gibco); penicillin G, 6 mg/100 ml (Sigma); streptomycin sulfate, 6 mg/ 100 ml (Sigma) and 10% fetal calf serum (Hyclone, Logan, Utah). Media is filtered through a 0.22 micron sterile syringe filter (Fisher, Santa Clara, Calif.) and equilibrated at 37° C. and 5% $CO_2$ in air prior to use. hCG (Pregnyl, Organon, W. Orange, N.J.) was added to the culture media in amounts as described below.

Extracellular matrix was applied to culture dishes according to the manufacturer's directions on the same day cells were collected. A thin layer (50 μl/well) of Matrigel (Collaborative Biomedical, Bedford, Mass.) is applied to the bottom of 4 well plates (Nunc) with a 100 μl pipette tip and rapidly spreading the Matrigel with the tip. All plates, matrigel and pipets are kept on ice during the coating procedure. Coated plates are incubated at 37° C. for 30 min in 5% $CO_2$ to set the Matrigel and were then ready for use.

Cell Collection

Human granulosa cells (GCs) were obtained by ultrasound-guided follicle aspiration from women receiving assisted reproduction treatment. Approximately 1.0 ml modified human Tubal Fluid Media (Irvine Scientific, Santa Ana, Calif.) containing HEPES buffer, antibiotics, and heparin, was added to the follicular fluid aspirate during the oocyte retrieval procedure. After oocytes and cumulus masses were removed, the follicular fluid containing granulosa cells was refrigerated and transported on ice to California Regional Primate Research Center in a 50 ml flask.

Culture Preparation

All cell preparation was performed under a laminar flow hood to maintain sterile conditions. Follicular fluid was divided equally into 15 ml disposable, sterile centrifuge tubes and centrifuged at 300×g for 5 min and then at 500×g for an additional 5 min. This created a firm layer of GCs on top of a red blood cell pellet. The layer of GCs were collected from each tube with a Pasteur pipette and combined in a sterile 15 ml centrifuge tube. About 4 ml MEM was added and the GCs were gently aspirated through a 1.0 ml disposable pipet tip to break up clumps. One ml aliquots of this cell suspension were layered onto 1.0 ml 40% Percoll (Sigma, St. Louis, Mo.) in PBS columns in 15 ml centrifuge tubes and centrifuged at 500×g for 30 min. The GC layer was removed from each Percoll column and combined in a sterile 15 ml centrifuge tube. Cells were washed twice with 5–10 ml fresh MEM and centrifuged for 10 min at 300×g. The supernatant was discarded and the pellet was resuspended in 2–4 ml of MEM (commercial/minimum essential medium eagle). GCs were filtered through an 89 micron polyester filter (Spectra/Mesh) just prior to being counted and plated.

Cells were counted on a hemacytometer and brought to a final concentration of $1 \times 10^5$ cells/ml in MEM and plated on 4 well plates (1.9 cm diameter wells) at $5 \times 10^4$ cells/well. Cells had attached after 24 hrs and media was changed to remove remaining debris. Media was changed daily in all experiments and stored frozen until assay for hormone concentrations.

hCG Protocol

A baseline concentration of 0.02 IU/ml was selected based upon its ability to provide good steroid and relaxin secretion. hCG concentrations were held at baseline hCG for each of the 20 days of culture. Media is changed daily.

VERIFICATION OF VIABILITY AND CELL NUMBER DURING CULTURE

Cells were prepared, plated and cultured as described above with multiple wells for each patient. Estimates of viability were obtained using trypan blue (0.4%, Gibco) exclusion on an Olympus CK2 microscope at 200 X. On the day cell number was to be verified, media was removed from the well and cells were rinsed 3 times with cold PBS (Sigma). One ml of Matrisperse (Fisher) was added to each well to free cells from the Matrigel and cells were scraped into a centrifuge tube. The well was rinsed with an additional 1 ml of Matrisperse which was placed in the tube and kept on ice for 1 hour.

Cells were centrifuged for 5 min at 500×g and pellet was resuspended in 100 mM PBS. Cells were counted on a hemacytometer.

Assays

Estradiol and progesterone were measured by commercial kits (Diagnostic Products Corp., Los Angeles, Calif.). Relaxin was measured by an enzyme immunoassay as previously reported for serum relaxin. The assay was modified by dilution of human relaxin using culture fluid instead of human serum for preparation of standards.

Data Analysis

Relaxin concentrations at day 10 of culture were used to determine if the cells are responders or nonresponders. Values of less than or equal to 200 pg/ml are considered nonresponders while relaxin concentrations >200 pg/ml are considered to be responders. If the relaxin concentrations are greater than 200 pg/ml the chances are that a successful pregnancy will result-noting that the probability of success increases to about 100% at relaxin concentration at or above 800 pg/ml. If relaxin concentrations are less than 200 pg/ml it indicates that either there will not be a conception or that the pregnancy will not continue to term.

It is possible that as more patients are examined, the current cutoff point of 200 pg/ml of relaxin on day 10 of culture will be modified. It is possible that a different concentration of relaxin will be more predictive. It is also possible that days other than day 10 of culture could be useful. Relaxin secretion begins about day 5 of culture and it is probable that differences would be significant by day 7 or 8 of culture if appropriate cutoff concentrations of relaxin are determined.

EXAMPLES 59 AND 60

Two human female patients underwent IVF and extracted granulosa cells were cultured as in Example 58 above. Both patients showed no detectable level of relaxin at day 10. Serum extracted from the patients over the same time also showed a corresponding level of relaxin. Neither patient conceived. These examples show a relationship between serum relaxin levels and levels in the cell culture per the present invention. This shows that low relaxin production in cell culture corresponds to abnormally low relaxin in circulation and that this lack is not compensated for by feedback mechanisms. This is also consistent with low circulating relaxin being a cause of failure to conceive or pregnancy loss.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of determining a probability of successful implantation with an ovarian stimulation in vitro fertilization and embryo transfer procedure, comprising:
    determining a relaxin level in a serum sample obtained from a patient who has undergone an ovarian stimulation in vitro fertilization and embryo transfer procedure; and
    determining a probability of successful implantation based on the patient's determined relaxin level;
    wherein a lower determined relaxin level relative to a standard relaxin level is associated with a decreased probability of successful implantation.

2. The method of claim 1, wherein measuring a relaxin level in serum is by an enzyme immunoassay.

* * * * *

UNITED STATES PATENT AND TRADEMARK OFFICE
CERTIFICATE OF CORRECTION

PATENT NO. : 6,660,531 B2  Page 1 of 1
DATED : December 9, 2003
INVENTOR(S) : Dennis R. Stewart It is certified that error appears in the above-identified patent and that said Letters Patent is hereby corrected as shown below:

<u>Title page,</u>
Item [75], Inventors, should read -- Dennis R. Stewart, Sacramento, CA (US). --

Signed and Sealed this

Twentieth Day of April, 2004

JON W. DUDAS
*Acting Director of the United States Patent and Trademark Office*